United States Patent [19]
Jamison et al.

[11] Patent Number: 5,618,787
[45] Date of Patent: Apr. 8, 1997

[54] CYCLIC PEPTIDE ANTIFUNGAL AGENTS

[75] Inventors: James A. Jamison; Michael J. Rodriguez, both of Indianapolis, Ind.

[73] Assignee: Eli Lilly and Company, Indianapolis, Ind.

[21] Appl. No.: 612,520

[22] Filed: Mar. 8, 1996

Related U.S. Application Data

[63] Continuation of Ser. No. 453,050, May 26, 1995, abandoned.

[51] Int. Cl.$^6$ .............................. A61K 38/12; C07K 5/00
[52] U.S. Cl. ................ 514/11; 514/9; 530/317; 424/93.5
[58] Field of Search ................ 530/317; 514/9, 514/11; 424/93.5

[56] References Cited

U.S. PATENT DOCUMENTS

| | | | |
|---|---|---|---|
| 4,293,488 | 10/1981 | Debono | 530/317 |
| 4,293,489 | 10/1981 | Debono | 530/317 |
| 4,320,052 | 3/1982 | Abbott et al. | 530/317 |
| 5,166,135 | 11/1992 | Schmatz | 514/11 |

FOREIGN PATENT DOCUMENTS

| | | |
|---|---|---|
| 0359529 | 3/1990 | European Pat. Off. . |
| 0448354 | 9/1991 | European Pat. Off. . |
| 0448356 | 9/1991 | European Pat. Off. . |
| 0448353 | 9/1991 | European Pat. Off. . |
| 0447186 | 9/1991 | European Pat. Off. . |
| 0448355 | 9/1991 | European Pat. Off. . |
| 0448343 | 9/1991 | European Pat. Off. . |
| 0462531 | 12/1991 | European Pat. Off. . |
| 0503960 | 9/1992 | European Pat. Off. . |
| 0525889 | 2/1993 | European Pat. Off. . |
| 561639 | 9/1993 | European Pat. Off. . |
| 2241956 | 9/1991 | United Kingdom . |
| 2242194 | 9/1991 | United Kingdom . |

Primary Examiner—Howard E. Schain
Attorney, Agent, or Firm—Janet T. McClain; David E. Boone

[57] ABSTRACT

Provided are pharmaceutical formulations, and methods of inhibiting fungal and parasitic activity using a compound of formula I

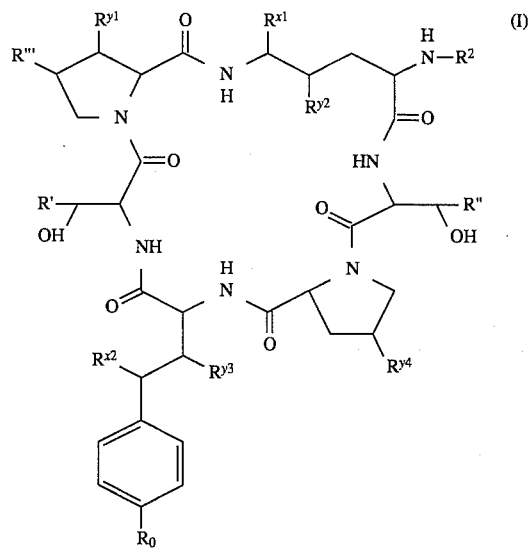

wherein:

R', R'', R''', $R^{x1}$, $R^{x2}$, $R^{y1}$, $R^{y2}$, $R^{y3}$, $R^{y4}$ and $R^0$ are as defined hereinabove; and $R^2$ is

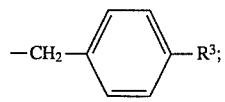

$R^3$ is

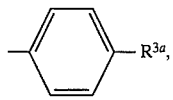

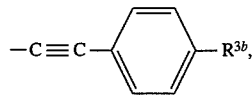

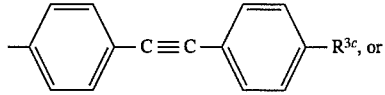

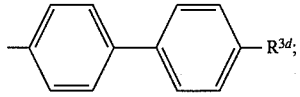

$R^{3a}$, $R^{3b}$, $R^{3c}$ and $R^{3d}$ are independently hydrogen, $C_1$–$C_{12}$ alkyl, $C_2$–$C_{12}$ alkynyl, $C_1$–$C_{12}$ alkoxy, $C_1$–$C_{12}$ alkylthio, halo, or —O—$(CH_2)_m$—[O—$(CH_2)_n]_p$—O—($C_1$–$C_{12}$ alkyl) or —O—$(CH_2)_q$—X—$R^4$;

m is 2, 3 or 4;

n is 2, 3 or 4;

p is 0 or 1;

q is 2, 3 or 4;

X is pyrrolidino, piperidino or piperazino; and $R^4$ is hydrogen, $C_1$–$C_{12}$ alkyl, $C_3$–$C_{12}$ cycloalkyl, benzyl or $C_3$–$C_{12}$ cycloalkylmethyl;

or a pharmaceutically acceptable salt thereof.

30 Claims, No Drawings

CYCLIC PEPTIDE ANTIFUNGAL AGENTS

This application is a continuation of application Ser. No. 08/453,050, filed on May 26, 1995 now abandoned.

BACKGROUND OF THE INVENTION

This invention relates to semi-synthetic cyclic peptide compounds which are useful as antifungal and antiparasitic agents and which have improved stability and water solubility. In particular, it relates to derivatives of the echinocandin class of cyclic peptides; to methods for treating fungal and parasitic infections, and to formulations useful in the methods.

The compounds provided by this invention are semi-synthetic compounds derived from cyclic peptides which are produced by culturing various microorganisms. A number of cyclic peptides are known in the art including echinocandin B (A30912A), aculeacin, mulundocandin, sporiofungin, L-671,329, and S31794/F1.

In general, these cyclic peptides may be structurally characterized as a cyclic hexapeptide core (or nucleus) with an acylated amino group on one of the core amino acids. The amino group is typically acylated with a fatty acid group forming a side chain off the nucleus. For example, echinocandin B has a linoleoyl side chain while aculeacin has a palmitoyl side chain.

The fatty acid side chains may be removed from the cyclic peptide core to provide an amino nucleus (for example, a compound of formula I, below, where $R_2$ is hydrogen). The amino group may then be re-acylated to provide semi-synthetic compounds such as those claimed in the present application.

The echinocandin B nucleus has been re-acylated with certain non-naturally occurring side chain moieties to provide a number of antifungal agents (see, Debono, U.S. Pat. No. 4,293,489). Among such antifungal agents is cilofungin which is represented by a compound of formula I where R', R", and R'" are methyl; $R^{x1}$, $R^{x2}$, $R^{y1}$, $R^{y2}$, $R^{y3}$, $R^{y4}$ and $R^0$ is hydroxy and $R^2$ is p-(octyloxy)benzoyl.

SUMMARY OF THE INVENTION

The present invention provides a compound of the formula:

(I)

wherein:
R' is hydrogen, methyl or —CH$_2$C(O)NH$_2$;
R" and R'" are independently methyl or hydrogen;
$R^{x1}$ is hydrogen, hydroxy or —O—R;
R is C$_1$–C$_6$ alkyl, benzyl, —(CH$_2$)$_2$Si(CH$_3$)$_3$, —CH$_2$CHOHCH$_2$OH, —CH$_2$CH=CH$_2$, —(CH$_2$)$_a$COOH, —(CH$_2$)$_b$NR$^{z1}$R$^{z2}$, —(CH$_2$)$_c$POR$^{z3}$R$^{z4}$ or —[(CH$_2$)$_2$O]$_d$—(C$_1$–C$_6$)alkyl;
a, b and c are independently 1, 2, 3, 4, 5 or 6;
$R^{z1}$ and $R^{z2}$ are independently hydrogen, C$_1$–C$_6$ alkyl, or $R^{z1}$ and $R^{z2}$ combine to form —CH$_2$(CH$_2$)$_e$CH$_2$—;
$R^{z3}$ and $R^{z4}$ are independently hydroxy or C$_1$–C$_6$ alkoxy;
d is 1 or 2;
e is 1, 2 or 3;
$R^{x2}$, $R^{y1}$, $R^{y2}$, $R^{y3}$ and $R^{y4}$ are independently hydroxy or hydrogen;
$R^0$ is hydroxy, —OP(O)(OH)$_2$ or a group of the formulae:

$$-O-\underset{OH}{\underset{|}{\overset{O}{\overset{\|}{P}}}}-R^1 \text{ or } -O-\underset{OH}{\underset{|}{\overset{O}{\overset{\|}{P}}}}-OR^1;$$

$R^1$ is C$_1$–C$_6$ alkyl, phenyl, p-halo-phenyl, p-nitrophenyl, benzyl, p-halo-benzyl or p-nitro-benzyl;
$R^2$ is —CH$_2$—⟨phenyl⟩—R$^3$;

$R^3$ is

—⟨phenyl⟩—R$^{3a}$,

—C≡C—⟨phenyl⟩—R$^{3b}$,

—⟨phenyl⟩—C≡C—⟨phenyl⟩—R$^{3c}$, or

—⟨phenyl⟩—⟨phenyl⟩—R$^{3d}$;

$R^{3a}$, $R^{3b}$, $R^{3c}$ and $R^{3d}$ are independently hydrogen, C$_1$–C$_{12}$ alkyl, C$_2$–C$_{12}$ alkynyl, C$_1$–C$_{12}$ alkoxy, C$_1$–C$_{12}$ alkylthio, halo, or —O—(CH$_2$)$_m$—[O—(CH$_2$)$_n$]$_p$—O—(C$_1$–C$_{12}$ alkyl) or —O—(CH$_2$)$_q$—X—R$^4$;
m is 2, 3 or 4;
n is 2, 3 or 4;
p is 0 or 1;
q is 2, 3 or 4;
X is pyrrolidino, piperidino or piperazino; and
$R^4$ is hydrogen, C$_1$–C$_{12}$ alkyl, C$_3$–C$_{12}$ cycloalkyl, benzyl or C$_3$–C$_{12}$ cycloalkylmethyl;
or a pharmaceutically acceptable salt thereof.

Also provided are pharmaceutical formulations, methods for inhibiting parasitic or fungal activity and methods of treating fungal or parasitic infections which employ the compounds of the invention.

DETAILED DESCRIPTION

As used herein, the term "$C_1$–$C_{12}$ alkyl" refers to a straight or branched alkyl chain having from one to twelve carbon atoms. Typical $C_1$–$C_{12}$ alkyl groups include methyl, ethyl, propyl, isopropyl, butyl, sec-butyl, t-butyl, pentyl, 5-methylpentyl, hexyl, heptyl, 3,3-dimethylheptyl, octyl, 2-methyl-octyl, nonyl, decyl, undecyl, dodecyl and the like. The term "$C_1$–$C_{12}$ alkyl" includes within its definition the terms "$C_1$–$C_6$ alkyl" and "$C_1$–$C_4$ alkyl."

The term "$C_2$–$C_{12}$ alkynyl" refers to a straight or branched alkynyl chain having from two to twelve carbon atoms. Typical $C_2$–$C_{12}$ alkynyl groups include ethynyl, 1-propyn-1-yl, 1-propyn-2-yl, 1-butyn-1-yl, 1-butyn-3-yl, 1-pentyn-3-yl, 4-pentyn-2-yl, 1-hexyn-3-yl, 3-hexyn-1-yl, 5-methyl-3-hexyn-1-yl, 5-octyn-1-yl, 7-octyn-1-yl, 4-decyn-1-yl, 6-decyn-1-yl and the like.

The term "halo" refers to chloro, fluoro, bromo or iodo.

The term "$C_1$–$C_{12}$ alkylthio" refers to a straight or branched alkyl chain having from one to twelve carbon atoms attached to a sulfur atom. Typical $C_1$–$C_{12}$ alkylthio groups include methylthio, ethylthio, propylthio, isopropylthio, butylthio, 3-methyl-heptylthio, octylthio, 5,5-dimethyl-hexylthio and the like.

The term "$C_1$–$C_{12}$ alkoxy" refers to a straight or branched alkyl chain having from one to twelve carbon atoms attached to an oxygen atom. Typical $C_1$–$C_{12}$ alkoxy groups include methoxy, ethoxy, propoxy, butoxy, sec-butoxy, pentoxy, 5-methyl-hexoxy, heptoxy, octyloxy, decyloxy dodecyloxy and the like. The term "$C_1$–$C_{12}$ alkyl" includes within its definition the terms "$C_1$–$C_6$ alkoxy" and "$C_1$–$C_4$ alkoxy."

The term "$C_3$–$C_{12}$ cycloalkyl" refers a saturated hydrocarbon ring structure having from three to twelve carbon atoms. Typical $C_3$–$C_{12}$ cycloalkyl groups include cyclopropyl, cyclobutyl, cyclopentyl, cyclohexyl and cycloheptyl, cyclooctyl and the like.

The term "hydroxy protecting group" refers to a substituent of an hydroxy group that is commonly employed to block or protect the hydroxy functionality while reactions are carried out on other functional groups on the compound. Examples of such hydroxy protecting groups include tetrahydropyranyl, 2-methoxyprop-2-yl, 1-ethoxyeth-1-yl, methoxymethyl, β-methoxyethoxymethyl, methylthiomethyl, t-butyl, t-amyl, trityl, 4-methoxytrityl, 4,4'-dimethoxytrityl, 4,4',4"-trimethoxytrityl, benzyl, allyl, trimethylsilyl, (t-butyl)dimethylsilyl, and 2,2,2-trichloroethoxycarbonyl and the like. The species of hydroxy protecting group is not critical so long as the derivatized hydroxy group is stable to the conditions of the subsequent reaction(s) and can be removed at the appropriate point without disrupting the remainder of the molecule. A preferred hydroxy protecting group is trimethylsilyl. Further examples of hydroxy protecting groups are described in T. W. Greene, "Protective Groups in Organic Synthesis," John Wiley and Sons, New York, N.Y., (2nd ed., 1991) chapters 2 and 3. The term "protected hydroxy" refers to a hydroxy group bonded to one of the above hydroxy protecting groups.

The term "amino protecting group" as used in the specification refers to substituents of the amino group commonly employed to block or protect the amino functionality while reacting other functional groups on the compound. Examples of such amino protecting groups include formyl, trityl, phthalimido, trichloroacetyl, chloroacetyl, bromoacetyl, iodoacetyl groups, or urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, t-butoxycarbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)-prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-4-toluylsulfonyl)ethoxycarbonyl, 2-(methylsulfonyl)ethoxycarbonyl, 2-(triphenylphosphino)-ethoxycarbonyl, fluorenylmethoxycarbonyl ("FMOC"), 2-(trimethylsilyl)ethoxycarbonyl, allyloxycarbonyl, 1-(trimethyisilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-decyloxy)benzyloxycarbonyl, isobornyloxycarbonyl, 1-piperidyloxycarbonyl and the like; benzoylmethylsulfonyl, 2-nitrophenylsulfenyl, diphenylphosphine oxide and like amino protecting groups. The species of amino protecting group employed is not critical so long as the derivatized amino group is stable to the condition of subsequent reaction(s) on other positions of the intermediate molecule and can be selectively removed at the appropriate point without disrupting the remainder of the molecule including any other amino protecting group(s). Preferred amino protecting groups are t-butoxycarbonyl (t-Boc), allyloxycarbonyl and benzyloxycarbonyl (CbZ). Further examples of groups referred to by the above terms are described by J. W. Barton, "Protective Groups in Organic Chemistry", J. G. W. McOmie, Ed., Plenum Press, New York, N.Y., 1973, Chapter 2, and T. W. Greene, "Protective Groups in Organic Synthesis", John Wiley and sons, New York, N.Y., 1981, Chapter 7.

The term "inhibiting", i.e. a method of inhibiting parasitic or fungal activity, includes stopping, retarding or prophylactically hindering or preventing the growth or any attending characteristics and results from the existence of a parasite or fungus.

The term "contacting", i.e. contacting a compound of the invention with a parasite or fungus, includes a union or junction, or apparent touching or mutual tangency of a compound of the invention with a parasite or fungus. However, the term does not imply any further limitations to the process, such as by mechanism of inhibition, and the methods are defined to encompass the spirit of the invention, which is to inhibit parasitic and fungal activity by the action of the compounds and their inherent antiparasitic and antifungal properties, or in other words, the compounds, used in the claimed methods are the causative agent for such inhibition.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a mineral or organic acid or an inorganic base. Such salts are known as acid addition and base addition salts.

Acids commonly employed to form acid addition salts are mineral acids such as hydrochloric acid, hydrobromic acid, hydroiodic acid, sulfuric acid, phosphoric acid and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, λ-hydroxybutyrate, glycollate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonames, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

Preferred compounds of this invention are those compounds of formula I where:

$R'$, $R''$ and $R'''$ are each methyl;
$R^{y1}$, $R^{y2}$, $R^{y3}$ and $R^{y4}$ are each hydroxy;
$R^{x1}$ is hydrogen, hydroxy or —O—R;
R is methyl, benzyl, —CH$_2$CHOHCH$_2$OH, —(CH$_2$)$_b$NR$^{z1}$R$^{z2}$ or —(CH$_2$)$_2$POR$^{z3}$R$^{z4}$;
b is 2, 3, 4, 5 or 6;
$R^{z1}$ and $R^{z2}$ are independently hydrogen or $C_1$–$C_4$ alkyl;
$R^{z3}$ and $R^{z4}$ are independently hydroxy or methoxy;
$R^{x2}$ is hydrogen or hydroxy;
$R^0$ is hydroxy, or a group of the formulae:

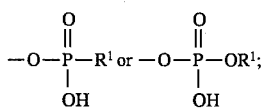

$R^1$ is methyl;
or a pharmaceutically acceptable salt thereof.

Of these compounds, more preferred are those compounds of formula I where:
$R^{x1}$ is hydroxy;
$R^{x2}$ is hydroxy;
$R^0$ is hydroxy;
$R^2$ is a group of the formula:

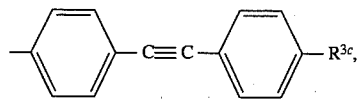

or

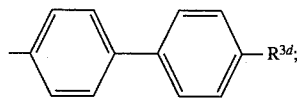

$R^{3c}$ and $R^{3d}$ are independently hydrogen, $C_2$–$C_{12}$ alkynyl, $C_1$–$C_{12}$ alkoxy or —O—(CH$_2$)$_m$—[O—(CH$_2$)$_n$]$_p$—O—(C$_1$–C$_{12}$ alkyl); or a pharmaceutically acceptable salt thereof.

Of these compounds, the most preferred are those compounds where
$R^2$ is

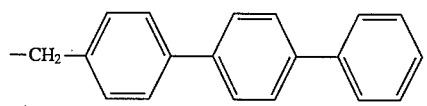

or
$R^2$ is

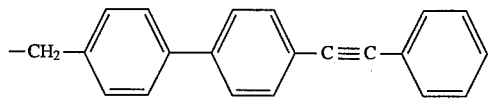

or a pharmaceutically acceptable salt thereof.

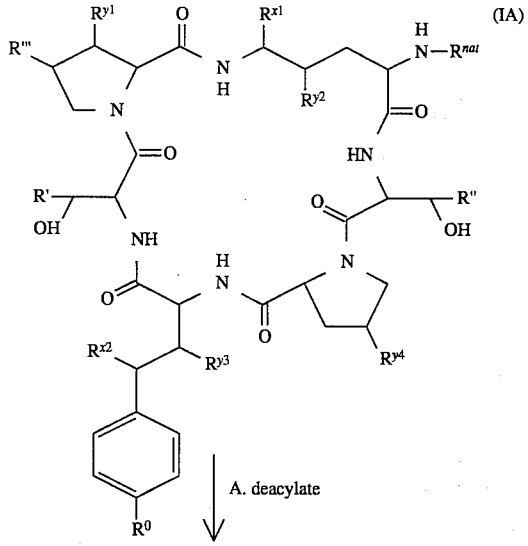

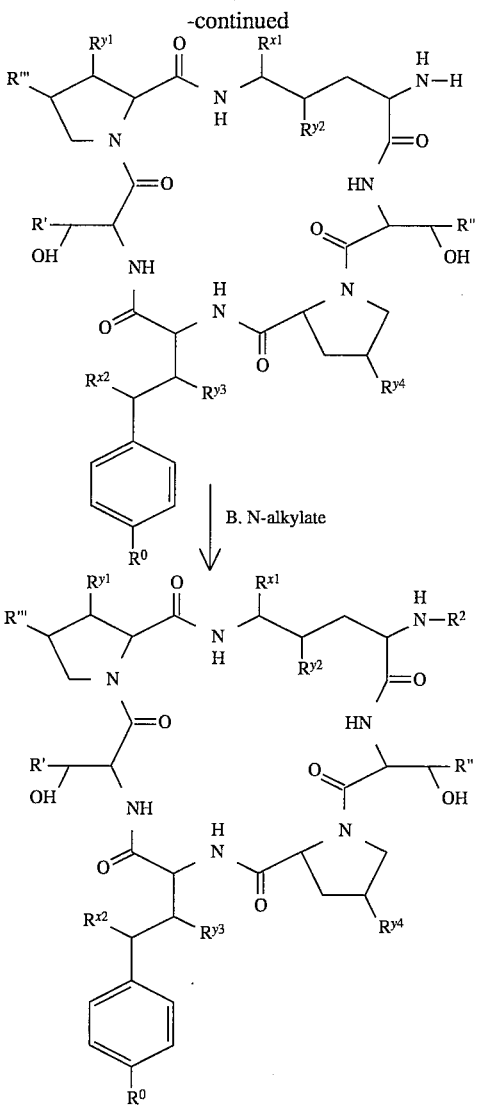

wherein:

$R^{nat}$ is a naturally occurring cyclic peptide sidechain; and R', R", R''', $R^{x1}$, $R^{x2}$, $R^{y1}$, $R^{y2}$, $R^{y3}$, $R^{y4}$, $R^0$ and $R^2$ are as defined above.

Reaction scheme I, above, is accomplished by carrying out reactions A–C, in order. Once a reaction is complete, the intermediate compound may be isolated by procedures well-known in the arm, for example, the compound may be crystallized or precipitated and then collected by filtration, or the reaction solvent may be removed by extraction, evaporation or decantation. The intermediate compound may be further purified, if desired, by common techniques such as crystallization or precipitation, or chromatography over solid supports such as silica gel, alumina and the like, before carrying out the next step of the reaction scheme.

In reaction IA, a naturally occurring cyclic peptide of the formula IA is deacylated using procedures known in the art to provide an amino nucleus of formula IB. This reaction is typically carried out using enzymatic deacylation by exposing the naturally occurring cyclic peptide to a deacylase enzyme. The deacylase enzyme may be obtained from the microorganism *Actinoplanes utahensis* and used substantially as described in U.S. Pat. Nos. 4,293,482 and 4,304,716, herein incorporated by reference. The deacylase enzyme may also be obtained from the *Pseudomonas* species. Deacylation may be accomplished using whole cells of *Actinoplanes utahensis* or *Pseudomonas* or the crude or purified enzyme thereof or using an immobilized form of the enzyme. See European Patent Application No. 0 460 882 (Dec. 11, 1991). Examples of naturally occurring cyclic peptides which may be used as starting materials include aculeacin (palmitoyl side chain), tetrahydroechinocandin B (stearoyl side chain), mulundocandin (branched $C_{15}$ side chain), L-671,329 ($C_{16}$ branched side chain), S 31794/F1 (tetradecanoyl side chain), sporiofungin ($C_{15}$ branched side chain), FR901379 (palmitoyl side chain) and the like. A preferred naturally occurring cyclic peptide is echinocandin B (a compound of formula IA where R', R" and R''' are each methyl, $R^{x1}$, $R^{x2}$, $R^{y1}$, $R^{y2}$, $R^{y3}$, $R^{y4}$ and $R^0$ are each hydroxy and $R^2$ is linoleoyl).

In Reaction IB, the resulting amino nucleus is N-alkylated using reductive amination to provide a compound of formula I where $R^2$ is as defined hereinabove. The reaction is typically carried out by reacting the amino nucleus of formula IB with an appropriately substituted aldehyde of the formula $R^2$-COH in the presence of a reducing agent such as sodium cyanoborohydride. The reaction is typically carried out for one to sixty five hours at a temperature of from about 20° C. to about 100° C. in a mutual inert solvent. Typical solvents for this reaction include dimethylformamide, methanol or a mixture of such solvents. Solvent choice is not critical so long as the solvent employed is inert to the ongoing reaction and the reactants are sufficiently solubilized to effect the desired reaction. The aldehyde reactant is generally employed in a slight excess relative to the amino nucleus.

The compounds of formula I where $R^{x1}$ is hydroxy may be reacted with an appropriately substituted alcohol in the presence of an acid to provide a compound of formula I where $R^{x1}$ is —O—R, where R is $C_1$–$C_6$ alkyl, benzyl, —$(CH_2)_2Si(CH_3)_3$, —$CH_2CH$=$CH_2$, —$(CH_2)_a COOH$, —$(CH_2)_b NR^{z1}R^{z2}$, —$(CH_2)_c POR^{z3}R^{z4}$ or —$[(CH_2)_2O]_d$—($C_1$–$C_6$) alkyl. The reaction is typically carried out in a polar aprotic solvent such as dioxane or dimethylsulfoxide at a temperature of from about 0° C. to about 35° C., preferably at about room temperature. Solvent choice is not critical so long as the solvent employed is inert to the ongoing reaction and the reactants are sufficiently solubilized to effect the desired reaction. Preferred acids include p-toluenesulfonic acid, hydrochloric acid and camphorsulfonic acid.

The compounds of formula I where $R^{x1}$ is —$(CH_2)_b NR^{z1}R^{z2}$ where $R^{z1}$ and $R^{z2}$ are hydrogen may be prepared via a protected compound wherein $R^{x1}$ is —$(CH_2)_b NHR^a$ where $R^a$ is an amino protecting group. The resultant protected compound is then deprotected according to procedures known in the art.

The compounds of formula I where $R^{x1}$ is —$CH_2CHOHCH_2OH$ may be prepared by hydroxylating a compound of formula I where $R^{x1}$ is —$CH_2CH$=$CH_2$ with osmium tetroxide in the presence of a catalyst at a temperature in the range of from about 0° C. to about 40° C. for about one to twenty four hours in a organic/aqueous solvent mixture, for example dioxane/water. Suitable catalysts include N-methylmorpholine N-oxide (NMO) and the like. Typical solvents suitable for use in this reaction include dimethylformamide, tetrahydrofuran, acetone and dioxane. Solvent choice is not critical so long as the solvent employed is inert to the ongoing reaction and the reactants are sufficiently solubilized to effect the desired reaction. The reaction is preferably conducted at a temperature in the range of from about 20° C. to about 30° C. for about eighteen to twenty four hours.

The compounds of formula I where $R^0$ is hydroxy may be phosphorylated by reaction with an appropriately substituted alkyl or phenyl phosphate to provide a compound of formula I where $R^0$ is —O—P(O)OH—$R^1$ where $R^1$ is $C_1$-$C_6$ alkoxy or phenoxy, or by reaction with an appropriately substituted alkyl or phenyl phosphonic acid to provide a compound of formula I where $R^0$ is —O—P(O)OH—$R^1$ where $R^1$ is $C_1$-$C_6$ alkyl, or an appropriately substituted phenyl or benzyl moiety, to provide a compound of formula I where $R^0$ is a group of the formula —OP/O)OH—$R^1$. The phosphonic acid is typically used in an activated form, for example as a phosphonic halide, preferably a phosphonic chloride. The reaction is carried out in the presence of a base such as lithium trimethylsilanolate (LiOTMS), lithium bis(trimethylsilyl)amide (LHMDS), pyridine and the like. The reaction is typically carried out for up to one hour at a temperature from about −30° C. to about 0° C. in an aprotic solvent such as tetrahydrofuran and dimethylformamide. The reaction is generally complete in about fifteen minutes when carried out under these conditions. The phosphate or phosphonate reactant is generally employed in equimolar proportions to about a one mole excess relative to the amino nucleus in the presence of an equimolar or slight excess of the base. Phosphorylation of an amino nucleus with unprotected aminal hydroxy groups is typically carried out at lower temperatures, for example from about −30° C. to about −15° C.

Alternatively, the aminal hydroxy moieties on the compound of formula I are optionally protected with an hydroxy protecting group using procedures known in the art. For example, the reaction is typically carried out by combining the compound of formula I with a suitable hydroxy protecting group in the presence of a catalyst at a temperature in the range of from about 0° C. to about 40° C. for about one to five hours in a mutual inert solvent. The hydroxy protecting group is generally employed in an amount ranging from about equimolar proportions to about a 100 molar excess relative to the compound of formula I, preferably in a large molar excess. Suitable catalysts include strong acids such as p-toluenesulfonic acid, camphorsulfonic acid (CSA), hydrochloric acid, sulfuric acid, trifluoroacetic acid and the like. Typical solvents suitable for use in this reaction include any organic solvent such as dioxane. Solvent choice is not critical so long as the solvent employed is inert to the ongoing reaction and the reactants are sufficiently solubilized to effect the desired reaction. The reaction is preferably conducted at a temperature in the range of from about 20° C. to about 30° C. for about two to four hours. The protected compound of formula I is then phosphorylated as described above. The hydroxy protecting group(s) are then removed according to procedures known in the art to provide a phosphorylated compound of formula I. For example, the protecting groups can be removed by reaction with a Lewis acid in a mutual inert organic solvent such as methylene chloride. Examples of Lewis acids include trimethylsilylbromide, boron trifluoride etherate and the like. The reaction is typically carried out at a temperature of from about 0° C. to about 40° C., preferably at a temperature of from about 20° C. to about 30° C. A preferred Lewis acid is boron trifluoride etherate.

The dideoxy compounds of formula I are prepared by removing the benzylic and aminal hydroxy groups ($R^{x2}$ and $R^{x1}$, respectively). The hydroxy groups may be removed by subjecting a non-dideoxy compound of formula I (where $R_2$ is hydrogen or acyl) to a strong acid and a reducing agent at a temperature of between −5° C. and 70° C., in a suitable solvent. Typical strong acids include trichloroacetic acid, trifluoroacetic acid or borontrifluoride etherate. A preferred strong acid is trifluoroacetic acid. Typical reducing agents include sodium cyanoborohydride or triethylsilane. A preferred reducing agent is triethylsilane. Suitable solvents include methylene chloride, chloroform or acetic acid, preferably methylene chloride. The strong acid should be present in an amount of from 2 to 80 mol per mol of substrate, and the reducing agent should be present in an amount of 2 to 80 mol per mol of substrate. This process affords selective removal of the aminal and benzylic hydroxy groups.

The cyclic peptides used to make the compounds of the present invention may be prepared by fermentation of known microorganisms. For example, the cyclic peptide of formula IB where R', R" and R'" are methyl, $R^{x1}$, $R^{x2}$, $R^{y1}$, $R^{y2}$, $R^{y3}$, $R^{y4}$ are hydroxy and $R^0$ is hydroxy (cyclic nucleus corresponding to A-30912A) may be prepared using the procedure detailed in Abbott et al., U.S. Pat. No. 4,293,482, which is herein incorporated by reference. The cyclic peptide of formula IB where R', R" and R'" are methyl, $R^{x1}$ is hydroxy, $R^{x2}$ is hydrogen, $R^{y1}$, $R^{y2}$, $R^{y3}$, $R^{y4}$ and $R^0$ is hydroxy (cyclic nucleus corresponding to A-30912B) may be prepared using the procedure detailed in Abbott et al., U.S. Pat. No. 4,299,763, which is herein incorporated by reference. Aculeacin may be prepared using the procedure detailed in Mizuno et al., U.S. Pat. No. 3,978,210 which is herein incorporated by reference. The cyclic peptide of formula IB where R' is —CH$_2$C(O)NH$_2$, R" is methyl, R'" is hydrogen, $R^{x1}$, $R^{x2}$, $R^{y1}$, $R^{y2}$, $R^{y3}$, $R^{y4}$ and $R^0$ is hydroxy may be prepared by deacylating the cyclic peptide prepared using the procedure detailed in Chen et al., U.S. Pat. No. 5,198,421, which is herein incorporated by reference.

The aldehydes of the formula $R^2$—COH, used in the reductive amination, may be obtained commercially or prepared according to procedures known in the art. For example, an appropriately substituted phenyl boronic acid or biphenyl boronic acid reactant may be reacted with a p-halobenzaldehyde reactant in the presence of a catalyst such as tetrakis(triphenylphosphine)palladium and an inorganic base such as potassium carbonate in a mutual inert organic solvent such as toluene at a temperature of from about 20° C. to the reflux temperature of the reaction mixture to provide the corresponding biphenyl aldehydes and terphenyl aldehydes used to prepare the compounds of formula I. The reaction is typically carried out with equimolar proportions of the boronic acid reactant and the p-benzaldehyde reactant, or a slight molar excess of the p-benzaldehyde reactant relative to the boronic acid reactant, and a 1–2 molar excess of the inorganic base. The reaction is generally complete after about four to about ten hours when carried out at reflux temperature in toluene.

The boronic acid reactant may be prepared by reacting an appropriately substituted halophenyl or halobiphenyl reactant with two equivalents of triisopropyl borate in the presence of an alkyl lithium, for example sec-butyl lithium, in a mutual inert solvent such as tetrahydrofuran. The alkyl lithium is typically employed in a slight molar excess relative to the halophenyl or halobiphenyl reactant. The alkyl lithium is typically combined with the solvent by dropwise addition at reduced temperatures (<−70° C.) and allowed to stir for approximately thirty minutes before the addition of the triisopropyl borate. The reaction is typically carried out initially at a temperature of from about −100° C. to about −50° C., preferably from about −75° C. to about −85° C. for thirty minutes to two hours and then warmed to room temperature and reacted for an additional one to three hours. The reaction is generally complete in from several minutes to about four hours. When the reaction is substantially complete, the boronic acid moiety is formed by the addition of an acid. A preferred acid is a 1N hydrochloric acid solution.

The R²-COH aldehydes having an acetylene moiety may be prepared by reacting an appropriately substituted acetylene reactant with an appropriately substituted phenyl or biphenyl reactant of the formula

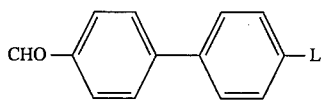

or

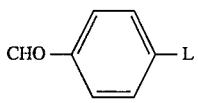

where L is a suitable leaving group such as bromo, iodo, methanesulfonate, toluenesulfonate, trifluoromethanesulfonate and the like, in the presence of a catalyst and preferably in the presence of an acid scavenger in a mutual inert solvent such as acetonitrile. Examples of acid scavengers include triethylamine and pyridine, preferably triethylamine. A preferred catalyst is formed in situ from palladium (II) chloride, triphenylphosphine and copper (I) iodide. The reaction is typically carried out for thirty minutes to twenty one hours at a temperature from about room temperature to the reflux temperature of reaction mixture. The reaction is generally complete after about two to about six hours when carried out at reflux temperature.

Alternatively, a suitably substituted phenyl reactant of the formula

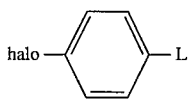

may be reacted with an appropriately substituted acetylene reactant as described above to provide, for example, a compound of the formula

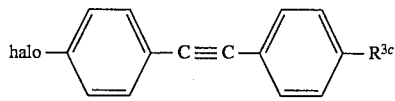

which can be coupled with a phenyl boronic acid reactant as described above.

The following Preparations and Examples further describe how to synthesize the compounds of the present invention. The terms melting point, proton nuclear magnetic resonance spectra, mass spectra, infrared spectra, ultraviolet spectra, elemental analysis, high performance liquid chromatography, and thin layer chromatography are abbreviated "m.p.", "NMR", "MS", "IR", "UV", "Analysis", "HPLC", and "TLC", respectively. In addition, the absorption maxima listed for the IR spectra are only those of interest and not all of the maxima observed.

Preparation 1

4-octyloxybenzaldehyde

A solution containing 3.053 g (25 mmol) of 4-formylphenol, 6.48 ml (3705 mmol) of 1-bromooctane and 6.9 mg (50 mmol) of potassium carbonate in 100 ml of acetone was refluxed overnight. When the reaction was substantially complete, as indicated by thin layer chromatagraphy (TLC), the reaction was quenched by the addition of 100 ml of water. The desired compound was extracted from the reaction mixture using two 100 ml portions of diethyl ether. The resultant solution was dried over magnesium sulfate, filtered and then concentrated in vacuo to provide a liquid which was purified using HPLC (eluent of 10 ethyl acetate in hexane) to provide the desired compound.
MS(FAB) : 235.2 (M+H).

Preparation 2

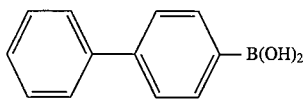
A.

To a cold (−78C) solution of 10.0 mg (42.9 mmol) of 1-bromo-4-phenylbenzene, was added 42.9 ml of a 1.3M solution of sec-butyllithium in tetrahydrofuran (55.8 mmol), dropwise. To the resultant mixture was added 14.85 ml (64.35 mmol) of triisopropyl borate, dropwise. The resultant reaction mixture was stirred for approximately thirty minutes and then warmed to room temperature and allowed to react for approximately two hours. The reaction was then quenched by the addition of approximately 50 ml of 1N hydrochloric acid and the resultant mixture was concentrated in vacuo to provide a residue. This residue was redissolved in diethyl ether, filtered and dried in vacuo to provide 1.58 g of the desired subtitled compound.

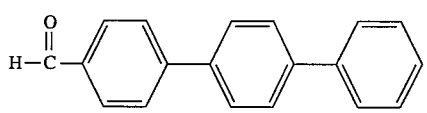
B.

A 2M solution of sodium carbonate was added to a solution of 2.970 g (15 mmol) of the compound of Preparation 2A in 120 ml of toluene. After degassing the resultant mixture, 3.470 g (18.75 mmol) of 1-bromo-4-formylbenzene and 1.713 g (1.5 mmol) of tetrakis(triphenylphosphine) palladium were added to the above solution and the resultant reaction mixture was refluxed overnight. When the reaction was substantially complete, as indicated by TLC, the reaction mixture was cooled to room temperature and concentrated in vacuo to provide a residue. This residue was redissolved in methylene chloride and washed with two 30 ml portions of brine. The organic portion was then filtered and dried in vacuo to provide a solid.

Preparation 3

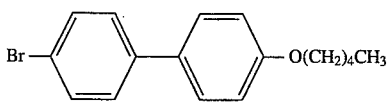
A.

A solution containing 50 g (200 mmol) of 4-bromophenol, 33.5 g (298 mmol) of potassium t-butoxide and 40 ml (298 mmol) of 1-iodopentane in 1000 ml of tetrahydrofuran was reacted at reflux temperature for approximately twenty four hours. When the reaction was substantially complete, as indicated by TLC, the reaction was filtered. The resultant filtrate was concentrated in vacuo to provide a purple solid. This solid was redissolved in a water/diethyl ether mixture to provide a yellow solution. This solution was washed sequentially with 200 ml of water (twice), 100 ml of 2N sodium hydroxide (twice) and 200 ml of brine (twice), dried over sodium sulfate and then concentrated in vacuo to provide a yellow powder. This solid was recrystallized from hot hexanes to provide a white powder.
Yield: 45.8 mg (72%).

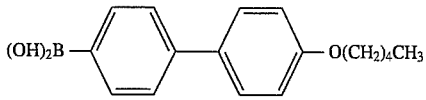 B.

To a cold (−78° C.) solution of 10.0 mg (42.9 mmol) of 29 g (90.8 mmol) of the compound of Preparation 1A, was added 91 ml of sec-butyllithium in 1000 ml of tetrahydrofuran (118 mmol), dropwise. To the resulting mixture was added 41.9 ml (181.7 mmol) of triisopropyl borate, dropwise. The resultant reaction mixture was stirred for approximately thirty minutes and then warmed to room temperature and allowed to react for approximately two hours. The reaction was then quenched by the addition of 1N hydrochloric acid. The resultant mixture was concentrated in vacuo to provide a residue. This residue was redissolved in diethyl ether, filtered and dried to provide the desired subtitled compound.
Yield:

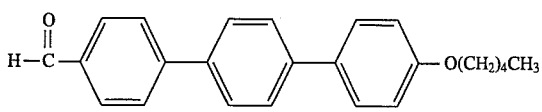 C.

A solution of 4.87 mg (26.2 mmol) of 1-bromo-4-formyl benzene in methanol was added to a solution containing 6 g (21 mmol) of the compound of Preparation 3B, 60 ml of 2M sodium carbonate and 2.5 g (2.1 mmol) of tetrakis(triphenylphosphine)palladium in 120 ml of toluene. The resultant reaction mixture was allowed to react at reflux temperature for approximately five hours. When the reaction was substantially complete, as indicated by TLC, the biphasic mixture was separated and the organic layer was washed sequentially with water and brine, dried over magnesium sulfate, filtered and concentrated in vacuo to provide a solid. This solid was recrystallized from hot hexanes.
MS(FD) : 344(M⁺).

Preparation 4

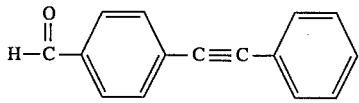

To a solution of 2.5 g (13 mmol) of p-bromo benzaldehyde in 16 ml of acetonitrile, was added 1.5 g (14 mmol) of phenyl acetylene, 0.55 g (0.52 mmol) of palladium-on-copper, 0.54 g (2 mmol) of triphenylphosphine, 0.1 g (0.52 mmol) of copper (I) iodide and 32.5 ml of triethylamine. The resultant reaction mixture was degassed in vacuo and flushed with argon (three times). After the reaction mixture was refluxed, under argon, for twenty four hours, the mixure was cooled to room temperature and concentrated in vacuo to provide a residue. This residue was purified using flash chromatography (silica gel; eluent of 20% ethyl acetete in hexanes) to provide 1 g of a white powder.
Yield: 37%.
$^1$H NMR (CDCl$_3$, 300 MHz):
δ 7.4 (m, 3H), 7.6 (m, 2H), 7.7 (d, J=7.68 Hz, 2H), 7.85 (d, J=7.68 Hz, 2H), 10.02 (s, 1H).

Preparation 5

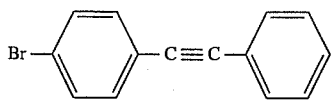 A.

To a solution containing 5 g (21.2 mmol) of 1,4-dibromobenzene, 18.8 mg (0.106 mmol) of palladium (II) chloride, 55.6 mg (0.212 mmol) of triphenylphosphine and 5.91 ml (0.726 mmol) of triethylamine in 300 ml of acetonitrile, was added 2.327 g (21.2 mmol) of phenyl acetylene and 40.0 mg (0.212 mmol) of copper (I) iodide. The resultant reaction mixture was allowed to react at room temperature for approximately two days. The crude material was purified using HPLC (eluent of hexane) to provide 660 mg of a white solid.

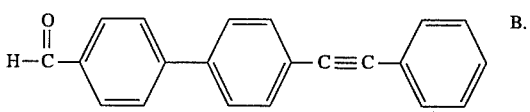 B.

The desired subtitled compound was prepared substantially in accordance with the procedure detailed in Preparation 2B, using 3.07 g (11.9 mmol) of the subtitled compound of Preparation 5A and 1.78 g 11.9 mmol) of 1-boronic acid-4-formylbenzene, 60 ml of 2M sodium carbonate and 1.360 g (1.19 mmol) of tetrakis(triphenylphosphine) palladium in 90 ml of toluene.
MS (FAB) : 283.1 (M+H).

EXAMPLE 1

Preparation of the compound of formula I where R', R" nd R'" are each methyl, $R^{x1}$, $R^{x2}$, $R^{y1}$, $R^{y2}$, $R^{y3}$, $R^{y4}$ and $R^0$ are each hydroxy and $R^2$ is 4-octyloxybenzyl A solution containing 1.5 g (1.88 mmol) of the (A-30912A) nucleus (compound of formula IB where R', R" and R'" are each methyl, $R^{x1}$, $R^{x2}$, $R^{y1}$, $R^{y2}$, $R^{y3}$, $R^{y4}$ and $R^0$ are each hydroxy), 697 mg (2.07 mmol) of the compound of Preparation 1, and 130 mg (2.07 mmol) of sodium cyanoborohydride in a 1:1 dimethylformamide/methanol mixture was heated at 70° C. overnight. When the reaction was substantially complete, as indicated by TLC, the reaction mixture was concentrated in vacuo the desired compound was isolated using HPLC (eluent of 40% aqueous acetonitrile; 60 ml/min.; 280 nm). The fractions containing the desired compound were combined and concentrated in vacuo to provide crude material. This material was purified using HPLC (eluent of 50% aqueous acetonitrile; 50 ml/min.; 280 nm).
Yield: 19 mg.
MS(FAB) for $C_{49}H_{72}N_7O_{15}$:
    Calcd: 998.5086 (M—H$_2$O);
    Found: 998.5076.

EXAMPLE 2

Preparation of the compound of formula I where R', R" and R'" are each methyl, $R^{x1}$, $R^{x2}$, $R^{y1}$, $R^{y2}$, $R^{y3}$, $R^{y4}$ and $R^0$ are each hydroxy and $R^2$ is

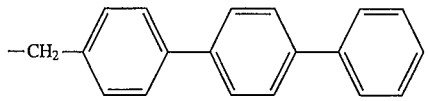

The desired compound was prepared substantially in accordance with the procedure detailed in Example 1 using 1.5 g (1.88 mmol) of the (A-30912A) nucleus (compound of formula IB where R', R" and R'" are each methyl, $R^{x1}$, $R^{x2}$, $R^{y1}$, $R^{y2}$, $R^{y3}$, $R^{y4}$ and $R^0$ is hydroxy), 533.5 mg (2.068 mmol) of the compound of Preparation 2B, and 130 mg (2.07 mmol) of sodium cyanoborohydride in 100 ml of a 1:1 dimethylformamide/methanol mixture with the exception that the reaction was substantially complete after approximately twelve hours. The crude material was purified using HPLC (eluent of 50% aqueous acetonitrile; 60 ml/min.; 280 nm).
Yield: 24 mg.
MS(FAB) for $C_{53}H_{65}N_7O_{15}$:
  Calcd: 1040.4617 (M+H);
  Found: 1040.4636.

EXAMPLE 3

Preparation of the compound of formula I where R', R" and R'" are each methyl, $R^{x1}$, $R^{x2}$, $R^{y1}$, $R^{y2}$, $R^{y3}$, $R^{y4}$ and $R^0$ are each hydroxy and $R^2$ is

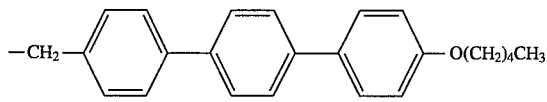

The desired compound was prepared substantially in accordance with the procedure detailed in Example 1 using 1 g (1.25 mmol) of the (A-30912A) nucleus (compound of formula IB where R', R" and R'" are each methyl, $R^{x1}$, $R^{x2}$, $R^{y1}$, $R^{y2}$, $R^{y3}$, $R^{y4}$ and $R^0$ is hydroxy), 474.0 mg (1.38 mmol) of the compound of Preparation 3C, and 86.7 mg (1.38 mmol) of sodium cyanoborohydride in 100 ml of a 3:1 merthanol/dimethylformamide mixture, with the exception that the reaction was substantially complete after approximately six hours. After isolating the crude material using HPLC (eluent of 50% aqueous acetonitrile; 60 ml/min.; 280 nm), the fractions containing the desired compound were combined, concentrated in vacuo and lyophilized.
MS(FAB) : 1132.5 (M+Li).

EXAMPLE 4A

Preparation of the compound of formula I where R', R" and R'" are each methyl, $R^{x2}$, $R^{y1}$, $R^{y2}$, $R^{y3}$, $R^{y4}$ and $R^0$ are each hydroxy, $R^{x1}$ is hydrogen, and $R^2$ is

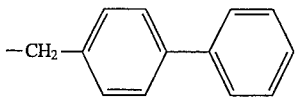

A solution of 203.0 mg (0.253 mmol) of the (A-30912A) nucleus (compound of formula IB where R', R" and R'" are each methyl, $R^{x1}$, $R^{x2}$, $R^{y1}$, $R^{y2}$, $R^{y3}$, $R^{y4}$ and $R^0$ is hydroxy) and 83.0 mg (0.455 mmol) of 4-phenylbenzaldehyde in 10 ml of methanol was reacted at reflux temperature.
Yield: 22 mg.
MS (FAB) for $C_{47}H_{61}N_7O_{15}$:
  Calcd: 964.4348 (M+H);
  Found: 964.4304.

EXAMPLE 4B

Alternate Preparation of the compound of formula I where R', R" and R'" are each methyl, $R^{x1}$, $R^{x2}$, $R^{y1}$, $R^{y2}$, $R^{y3}$, $R^{y4}$ and $R^0$ are each hydroxy and $R^2$ is

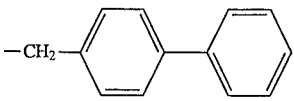

A solution of 1.5 g (1.88 mmol) of the (A-30912A) nucleus (compound of formula IB where R', R" and R'" are each methyl, $R^{x1}$, $R^{x2}$, $R^{y1}$, $R^{y2}$, $R^{y3}$, $R^{y4}$ and $R^0$ are each hydroxy), 376.8 mg (2.068 mmol) of 4-phenylbenzaldehyde and 130 mg (2.07 mmol) of sodium cyanoborohydride in a 100 ml of a 3:1 methanol/dimethylformamide mixture was allowed to react overnight at reflux temperature. The resultant crude material was isolated using HPLC (eluent of 50% aqueous acetonitrile; 60 ml/min.; 280 nm).
Yield: 68 mg.
MS(FAB) for $C_{47}H_{62}N_7O_{15}$:
  Calcd: 964.4304 (M+H);
  Found: 964.4348.

EXAMPLE 5

Preparation of the compound of formula I where R', R" and R'" are each methyl, $R^{x1}$, $R^{x2}$, $R^{y1}$, $R^{y2}$, $R^{y3}$, $R^{y4}$, and $R^0$ are each hydroxy and $R^2$ is

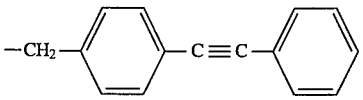

The desired compound was prepared substantially in accordance with the procedure detailed in Example 4A, using 375.3 mg (0.495 mmol) of the (A-30912A) nucleus (compound of formula IB where R', R" and R'" are each methyl, $R^{x1}$, $R^{x2}$, $R^{y1}$, $R^{y2}$, $R^{y3}$, $R^{y4}$ and $R^0$ are each hydroxy) and 158.3 mg (0.767 mmol) of the compound of Preparation 4 in 10 ml of ethanol.
Yield: 28 mg.
MS (FAB) for $C_{49}H_{60}N_7O_{14}$:
　Calcd: 970.4198 (M+H–H$_2$O);
　Found: 970.4222.

EXAMPLE 6

Preparation of the compound of formula I where R', R" and R'" are each methyl, $R^{x1}$, $R^{x2}$, $R^{y1}$, $R^{y2}$, $R^{y3}$, $R^{y4}$, and $R^0$ are each hydroxy and $R^2$ is

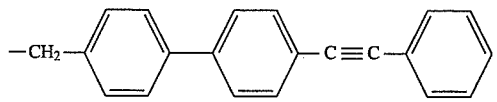

The desired compound was prepared substantially in accordance with the procedure detailed in Example 4A, using 577.8 mg (0.649 mmol) of the (A-30912A) nucleus (compound of formula IB where R', R" and R'" are each methyl, $R^{x1}$, $R^{x2}$, $R^{y1}$, $R^{y2}$, $R^{y3}$, $R^{y4}$ and $R^0$ is hydroxy) and 164.6 mg (0.583 mmol) of the compound of Preparation 5B in 10 ml of ethanol.
Yield: 51 mg.
MS(FAB) for $C_{55}H_{64}N_7O_{14}$:
　Calcd: 1046.4511 (M–H$_2$O);
　Found: 1046.4530.

The compounds of formula I exhibit antifungal and antiparasitic activity. For example, the compounds of formula I inhibit the growth of various infectious fungi including Candida spp. such as *C. albicans, C. parapsilosis, C. krusei, C. glabrata,* or *C. tropicalis, C. lusitaniae;* Torulopus spp. such as *T. glabrata;* Aspergillus spp. such as *A. fumigatus;* Histoplasma spp. such as *H. capsulatum;* Cryptococcus spp. such as *C. neoformans;* Blastomyces spp. such as *B. dermatitidis;* Fusarium spp., Trichophyton spp., *Pseudallescheria boydii, Coccidioides immitis, Sporothrix schenckii* and the like.

Antifungal activity of a test compound is determined in vitro by obtaining the minimum inhibitory concentration (MIC) of the compound using a standard agar dilution test or a disc-diffusion test. The compound is then tested in vivo (in mice) to determine the effective dose of the test compound for controlling a systemic fungal infection.

Accordingly, the following compounds were tested for antifungal activity against *C. albicans.*

TABLE 5

| Minimal inhibitory concentration against *C. albicans* | |
| --- | --- |
| Example No. | MIC (μg/ml) |
| 1 | 0.039 |
| 2 | 0.005 |
| 3 | 5.0 |
| 4 | 0.312 |
| 5 | 20 |
| 6 | 0.039 |

In addition, the effective dose of the following compounds for controlling a systemic fungal infection (*C. albicans*) was tested in vivo (mice).

TABLE 5-continued

| ED$_{50}$ (mouse) | |
| --- | --- |
| Example No. | ED$_{50}$ (mg/kg) |
| 1 | 63 |
| 2 | >20 |
| 3 | N.T. |
| 4 | >2.5 |
| 5 | >2.5 |
| 6 | >2.5 |

N.T. not tested

The compounds of the invention also inhibit the growth of certain organisms primarily responsible for opportunistic infections in immunosuppressed individuals. For example the compounds of the invention inhibit the growth of *Pneumocystis carinii* the causative organism of pneumocystis pneumonia (PCP) in AIDS and other immunocompromised patients. Other protozoans that are inhibited by compounds of formula I include Plasmodium spp., Leishmania spp., Trypanosoma spp., Cryptosporidium spp., Isospora spp., Cyclospora spp., Trichomonas spp., Microsporidiosis spp. and the like.

The compounds of formula I are active in vitro and in vivo and are useful in combating either systemic fungal infections or fungal skin infections. Accordingly, the present invention provides a method of inhibiting fungal activity comprising contacting a compound of formula I, or a pharmaceutically acceptable salt thereof, with a fungus. A preferred method includes inhibiting *Candida albicans* or *Aspergillus fumigatis* activity. The present invention further provides a method of treating a fungal infection which comprises administering an effective amount of a compound of formula I, or a pharmaceutically acceptable salt thereof, to a host in need of such treatment. A preferred method includes treating a *Candida albicans* or *Aspergillus fumigatis* infection.

With respect to antifungal activity, the term "effective amount," means an amount of a compound of the present invention which is capable of inhibiting fungal activity. The dose administered will vary depending on such factors as the nature and severity of the infection, the age and general health of the host and the tolerance of the host to the antifungal agent. The particular dose regimen likewise may vary according to such factors and may be given in a single daily dose or in multiple doses during the day. The regimen may last from about 2–3 days to about 2–3 weeks or longer. A typical daily dose (administered in single or divided doses) will contain a dosage level of from about 0.01 mg/kg to about 100 mg/kg of body weight of an active compound of this invention. Preferred daily doses generally will be from about 0.1 mg/kg to about 60 mg/kg and ideally from about 2.5 mg/kg to about 40 mg/kg.

The present invention also provides pharmaceutical formulations useful for administering the antifungal compounds of the invention. Accordingly, the present invention also provides a pharmaceutical formulation comprising one or more pharmaceutically acceptable carriers, diluents or excipients and a compound of claim 1. The active ingredient in such formulations comprises from 0.1% to 99.9% by weight of the formulation, more generally from about 10% to about 30% by weight. By "pharmaceutically acceptable" it is meant that the carrier, diluent or excipient is compatible with the other ingredients of the formulation and not deleterious to the recipient thereof.

A compound of formula I may be administered parentorally, for example using intramuscular, sub-cutaneous, or intra-peritoneal injection, nasal, or oral means. In addition to these methods of administration, a compound of formula I may be applied topically for skin infections.

For parentoral administration the formulation comprises a compound of formula I and a physiologically acceptable diluent such as deionized water, physiological saline, 5% dextrose and other commonly used diluents. The formulation may contain a solubilizing agent such as a polyethylene glycol or polypropylene glycol or other known solubilizing agent. Such formulations may be made up in sterile vials containing the antifungal and excipient in a dry powder or lyophilized powder form. Prior to use, a physiologically acceptable diluent is added and the solution withdrawn via syringe for administration to the patient.

The present pharmaceutical formulations are prepared by known procedures using known and readily I0 available ingredients. In making the compositions of the present invention, the active ingredient will generally be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), ointments containing, for example, up to 10% by weight of the active compound, soft and hard gelatin capsules, suppositories, sterile injectable solutions, sterile packaged powders and the like.

For oral administration, the antifungal compound is filled into gelatin capsules or formed into tablets. Such tablets may also contain a binding agent, a dispersant or other suitable excipients suitable for preparing a proper size tablet for the dosage and particular antifungal compound of the formula I. For pediatric or geriatric use the antifungal compound may be formulated into a flavored liquid suspension, solution or emulsion. A preferred oral formulation is linoleic acid, cremophor RH-60 and water and preferably in the amount (by volume) of 8% linoleic acid, 5% cremophor RH-60, 87% sterile water and a compound of formula I in an amount of from about 2.5 to about 40 mg/ml.

For topical use the antifungal compound may be formulated with a dry powder for application to the skin surface or it may be formulated in a liquid formulation comprising a solubilizing aqueous liquid or non-aqueous liquid, e.g., an alcohol or glycol.

The following formulation examples are illustrative only and are not intended to limit the scope of the invention in any way. The term "active ingredient" means a compound according to formula I or a pharmaceutically acceptable salt thereof.

FORMULATION 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

FORMULATION 2

A tablet is prepared using the ingredients below:

|  | Quantity (mg/capsule) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

FORMULATION 3

An aerosol solution is prepared containing the following components:

|  | Weight |
| --- | --- |
| Active ingredient | 0.25 |
| Methanol | 25.75 |
| Propellant 22 | 74.00 |
| (Chlorodifluoromethane) | |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

FORMULATION 4

Tablets, each containing 60 mg of active ingredient, are made as follows:

| Active ingredient | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinyl-pyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

FORMULATION 5

Capsules, each containing 80 mg of active ingredient, are made as follows:

| Active ingredient | 80 mg |
|---|---|
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

FORMULATION 6

Suppositories, each containing 225 mg of active ingredient, are made as follows:

| Active ingredient | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

FORMULATION 7

Suspensions, each containing 50 mg of active ingredient per 5 ml dose, are made as follows:

| Active ingredient | 50 mg |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

FORMULATION 8

An intravenous formulation may be prepared as follows:

| Active ingredient | 100 mg |
|---|---|
| Isotonic saline | 1,000 ml |

The solution of the above ingredients generally is administered intravenously to a subject at a rate of 1 ml per minute.

The present invention further provides a method for treating or preventing the onset of Pneumocystis pneumonia in a host susceptible to Pneumocystis pneumonia which comprises administering an effective amount of a compound of formula I, or a pharmaceutically acceptable salt thereof, to a host in need of such treatment. The compounds of formula I can be used prophylactically to prevent the onset of the infection which is caused by the organism *Pneumocystis carinii*, or alternatively they can be used to treat a host that has been infected with *P. carinii*. A compound of formula I may be administered parenterally, for example using intramuscular, intravenous or intra-peritoneal injection, orally or by inhaling directly into the airways of the lungs. A preferred mode of administration is inhalation of an aerosol spray formulation of a compound of formula I.

With respect to antiparasitic activity, the term "effective amount," means an amount of a compound of the present invention which is capable of inhibiting parasitic activity. An effective amount of the compound of formula I is from about 3 mg/kg of patient body weight to about 100 mg/kg. The amount administered may be in a single daily dose or multiple doses of, for example, two, three or four times daily throughout the treatment regimen. The amount of the individual doses, the route of delivery, the frequency of dosing and the term of therapy will vary according to such factors as the intensity and extent of infection, the age and general health of the patient, the response of the patient to therapy and how well the patient tolerates the drug. It is known that Pneumocystis pneumonia infections in AIDS patients are highly refractory owing to the nature of the infection. For example, in severe, advanced infections the lumenal surface of the air passages becomes clogged with infectious matter and extensive parasite development occurs in lung tissue. A patient with an advanced infection will accordingly require higher doses for longer periods of time. In contrast, immune deficient patients who are not severely infected and who are susceptible to Pneumocystis pneumonia can be treated with lower and less frequent prophylactic doses.

We claim:

1. A compound of the formula:

wherein:

$R'$ is hydrogen, methyl or —$CH_2C(O)NH_2$;

$R''$ and $R'''$ are independently methyl or hydrogen;

$R^{x1}$ is hydrogen, hydroxy or —O—R;

R is $C_1$–$C_6$ alkyl, benzyl, —$(CH_2)_2Si(CH_3)_3$, —$CH_2CHOHCH_2OH$, —$CH_2CH$=$CH_2$, —$(CH_2)_aCOOH$, —$(CH_2)_bNR^{z1}R^{z2}$, —$(CH_2)_cPOR^{z3}R^{z4}$ or —$[(CH_2)_2O]_d$—$(C_1$–$C_6)$alkyl;

a, b and c are independently 1, 2, 3, 4, 5 or 6;

$R^{z1}$ and $R^{z2}$ are independently hydrogen, $C_1$–$C_6$ alkyl, or $R^{z1}$ and $R^{z2}$ combine to form —$CH_2(CH_2)_eCH_2$—;

$R^{z3}$ and $R^{z4}$ are independently hydroxy or $C_1$–$C_6$ alkoxy;

d is 1 or 2;

e is 1, 2 or 3;

$R^{x2}$, $R^{y1}$, $R^{y2}$, $R^{y3}$ and $R^{y4}$ are independently hydroxy or hydrogen;

$R^0$ is hydroxy, —OP(O)(OH)$_2$ or a group of the formulae:

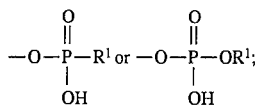

$R^1$ is $C_1$–$C_6$ alkyl, phenyl, p-halo-phenyl, p-nitrophenyl, benzyl, p-halo-benzyl or p-nitro-benzyl;

$R^2$ is

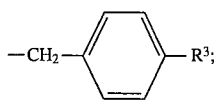

$R^3$ is

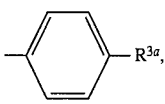

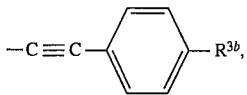

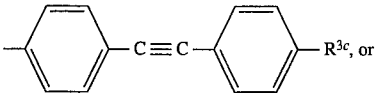

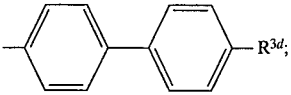

$R^{3a}$, $R^{3b}$, $R^{3c}$ and $R^{3d}$ are independently hydrogen, $C_1$–$C_{12}$ alkyl, $C_2$–$C_{12}$ alkynyl, $C_1$–$C_{12}$ alkoxy, $C_1$–$C_{12}$ alkylthio, halo, or —O—(CH$_2$)$_m$—[O—(CH$_2$)$_n$]$_p$—O—($C_1$–$C_{12}$ alkyl) or —O—(CH$_2$)$_q$—X—R$^4$;

m is 2, 3 or 4;

n is 2, 3 or 4;

p is 0 or 1;

q is 2, 3 or 4;

X is pyrrolidino, piperidino or piperazino; and $R^4$ is hydrogen, $C_1$–$C_{12}$ alkyl, $C_3$–$C_{12}$ cycloalkyl, benzyl or $C_3$–$C_{12}$ cycloalkylmethyl;

or a pharmaceutically acceptable salt thereof.

2. A compound according to claim 1 where:

R', R" and R'" are each methyl;

$R^{y1}$, $R^{y2}$, $R^{y3}$ and $R^{y4}$ are each hydroxy;

$R^{x1}$ is hydrogen, hydroxy or —O—R;

R is methyl, benzyl, —CH$_2$CHOHCH$_2$OH, —(CH$_2$)$_b$NR$^{z1}$R$^{z2}$ or —(CH$_2$)$_2$POR$^{z3}$R$^{z4}$;

b is 2, 3, 4, 5 or 6;

$R^{z1}$ and $R^{z2}$ are independently hydrogen or $C_1$–$C_4$ alkyl;

$R^{z3}$ and $R^{z4}$ are independently hydroxy or methoxy;

$R^{x2}$ is hydrogen or hydroxy;

$R^0$ is hydroxy or a group of the formulae:

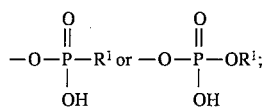

$R^1$ is methyl;

or a pharmaceutically acceptable salt thereof.

3. A compound according to claim 2 where:

$R^{x1}$ is hydroxy;

$R^{x2}$ is hydroxy;

$R^0$ is hydroxy;

$R^2$ is a group of the formula:

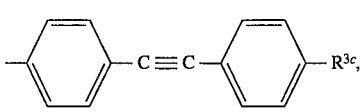

or

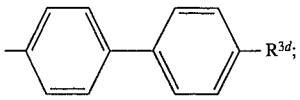

$R^{3c}$ and $R^{3d}$ are independently hydrogen, $C_2$–$C_{12}$ alkynyl, $C_1$–$C_{12}$ alkoxy or —O—(CH$_2$)$_m$—[O—(CH$_2$)$_n$]$_p$—O—($C_1$–$C_{12}$ alkyl);

or a pharmaceutically acceptable salt thereof.

4. The compound according to claim 3 where $R^2$ is

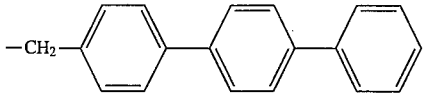

or a pharmaceutically acceptable salt thereof.

5. The compound according to claim 3 where $R^2$ is

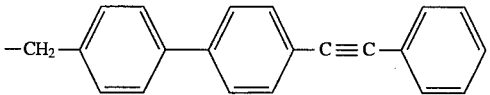

or a pharmaceutically acceptable salt thereof.

6. A pharmaceutical formulation comprising one or more pharmaceutically acceptable carriers, diluents or excipients and a compound of claim 1.

7. A pharmaceutical formulation according to claim 6 where the compound is one where:

R', R" and R'" are each methyl;

$R^{y1}$, $R^{y2}$, $R^{y3}$ and $R^{y4}$ are each hydroxy;

$R^{x1}$ is hydrogen, hydroxy or —O—R;

R is methyl, benzyl, —CH$_2$CHOHCH$_2$OH, —(CH$_2$)$_b$NR$^{z1}$R$^{z2}$ or —(CH$_2$)$_2$POR$^{z3}$R$^{z4}$;

b is 2, 3, 4, 5 or 6;

$R^{z1}$ and $R^{z2}$ are independently hydrogen or $C_1$–$C_4$ alkyl;

$R^{z3}$ and $R^{z4}$ are independently hydroxy or methoxy;

$R^{x2}$ is hydrogen or hydroxy;

$R^0$ is hydroxy or a group of the formulae:

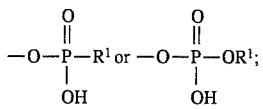

$R^1$ is methyl;
or a pharmaceutically acceptable salt thereof.

8. A pharmaceutical formulation according to claim 7 where the compound is one where:
$R^{x1}$ is hydroxy;
$R^{x2}$ is hydroxy;
$R^0$ is hydroxy;
$R^2$ is a group of the formula:

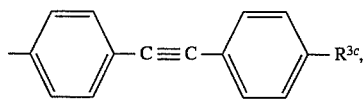

or

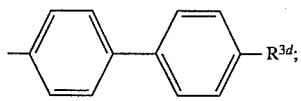

$R^{3c}$ and $R^{3d}$ are independently hydrogen, $C_2$–$C_{12}$ alkynyl, $C_1$–$C_{12}$ alkoxy or —O—$(CH_2)_m$—[O—$(CH_2)_n]_p$—O—($C_1$–$C_{12}$ alkyl);
or a pharmaceutically acceptable salt thereof.

9. The pharmaceutical formulation according to claim 8 where the compound is one where:
$R^2$ is

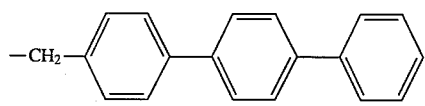

or a pharmaceutically acceptable salt thereof.

10. The pharmaceutical formulation according to claim 8 where the compound is one where:
$R^2$ is

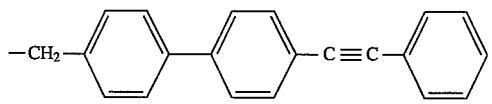

or a pharmaceutically acceptable salt thereof.

11. A method of inhibiting fungal activity comprising contacting a compound of claim 1 with a fungus.

12. A method according to claim 11 where the compound is one where:
R', R'' and R''' are each methyl;
$R^{y1}$, $R^{y2}$, $R^{y3}$ and $R^{y4}$ are each hydroxy;
$R^{x1}$ is hydrogen, hydroxy or —O—R;
R is methyl, benzyl, —$CH_2CHOHCH_2OH$, —$(CH_2)_b NR^{z1}R^{z2}$ or —$(CH_2)_2 POR^{z3}R^{z4}$;
b is 2, 3, 4, 5 or 6;
$R^{z1}$ and $R^{z2}$ are independently hydrogen or $C_1$–$C_4$ alkyl;
$R^{z3}$ and $R^{z4}$ are independently hydroxy or methoxy;
$R^{x2}$ is hydrogen or hydroxy;

$R^0$ is hydroxy or a group of the formulae:

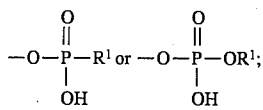

$R^1$ is methyl;
or a pharmaceutically acceptable salt thereof.

13. A method according to claim 12 where the compound is one where:
$R^{x1}$ is hydroxy;
$R^{x2}$ is hydroxy;
$R^0$ is hydroxy;
$R^2$ is a group of the formula:

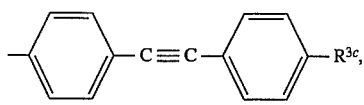

or

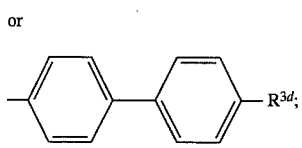

$R^{3c}$ and $R^{3d}$ are independently hydrogen, $C_2$–$C_{12}$ alkynyl, $C_1$–$C_{12}$ alkoxy or —O—$(CH_2)_m$—[O—$(CH_2)_n]_p$—O—($C_1$–$C_{12}$ alkyl);
or a pharmaceutically acceptable salt thereof.

14. The method according to claim 13 where the compound is one where:
$R^2$ is

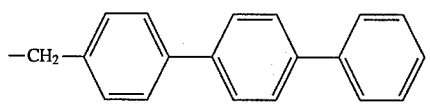

or a pharmaceutically acceptable salt thereof.

15. The method according to claim 13 where the compound is one where:
$R^2$ is

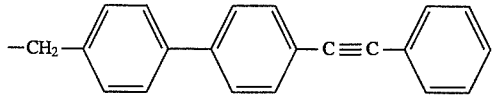

or a pharmaceutically acceptable salt thereof.

16. A method of treating a fungal infection which comprises administering an effective amount of a compound of claim 1 to a host in need of such treatment.

17. A method according to claim 16 where the compound is one where:
R', R'' and R''' are each methyl;
$R^{y1}$, $R^{y2}$, $R^{y3}$ and $R^{y4}$ are each hydroxy;
$R^{x1}$ is hydrogen, hydroxy or —O—R;
R is methyl, benzyl, —$CH_2CHOHCH_2OH$, —$(CH_2)_b NR^{z1}R^{z2}$ or —$(CH_2)_2 POR^{z3}R^{z4}$;
b is 2, 3, 4, 5 or 6;
$R^{z1}$ and $R^{z2}$ are independently hydrogen or $C_1$–$C_4$ alkyl;
$R^{z3}$ and $R^{z4}$ are independently hydroxy or methoxy;
$R^{x2}$ is hydrogen or hydroxy;

$R^0$ is hydroxy or a group of the formulae:

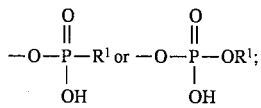

$R^1$ is methyl;
or a pharmaceutically acceptable salt thereof.

18. A method according to claim 17 where the compound is one where:

$R^{x1}$ is hydroxy;
$R^{x2}$ is hydroxy;
$R^0$ is hydroxy;
$R^2$ is a group of the formula:

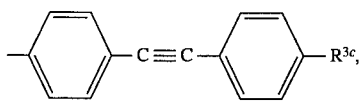

or

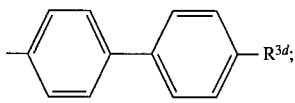

$R^{3c}$ and $R^{3d}$ are independently hydrogen, $C_2$–$C_{12}$ alkynyl, $C_1$–$C_{12}$ alkoxy or —O—$(CH_2)_m$[—O—$(CH_2)_n$]$_p$—O—($C_1$–$C_{12}$ alkyl);

or a pharmaceutically acceptable salt thereof.

19. The method according to claim 18 where the compound is one where:

$R^2$ is

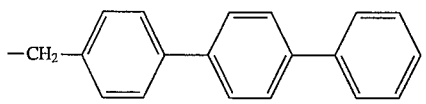

or a pharmaceutically acceptable salt thereof.

20. The method according to claim 18 where the compound is one where:

$R^2$ is

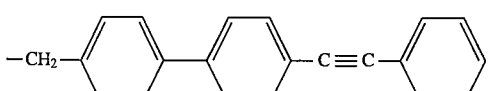

or a pharmaceutically acceptable salt thereof.

21. A method for inhibiting parasitic activity comprising contacting a compound of claim 1 with a parasite.

22. A method according to claim 21 where the compound is one where:

R', R" and R'" are each methyl;
$R^{y1}$, $R^{y2}$, $R^{y3}$ and $R^{y4}$ are each hydroxy;
$R^{x1}$ is hydrogen, hydroxy or —O—R;
R is methyl, benzyl, —$CH_2CHOHCH_2OH$, —$(CH_2)_b NR^{z1}R^{z2}$ or —$(CH_2)_2 POR^{z3}R^{z4}$;
b is 2, 3, 4, 5 or 6;
$R^{z1}$ and $R^{z2}$ are independently hydrogen or $C_1$–$C_4$ alkyl;
$R^{z3}$ and $R^{z4}$ are independently hydroxy or methoxy;
$R^{x2}$ is hydrogen or hydroxy;

$R^0$ is hydroxy or a group of the formulae:

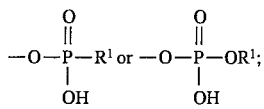

$R^1$ is methyl;
or a pharmaceutically acceptable salt thereof.

23. A method according to claim 22 where the compound is one where:

$R^{x1}$ is hydroxy;
$R^{x2}$ is hydroxy;
$R^0$ is hydroxy;
$R^2$ is a group of the formula:

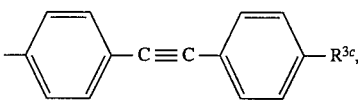

or

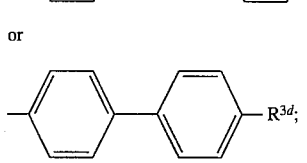

$R^{3c}$ and $R^{3d}$ are independently hydrogen, $C_2$–$C_{12}$ alkynyl, $C_1$–$C_{12}$ alkoxy or —O—$(CH_2)_m$—[O—$(CH_2)_n$]$_p$—O—($C_1$–$C_{12}$ alkyl);

or a pharmaceutically acceptable salt thereof.

24. The method according to claim 23 where the compound is one where:

$R^2$ is

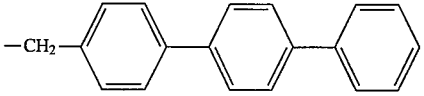

or a pharmaceutically acceptable salt thereof.

25. The method according to claim 23 where the compound is one where:

$R^2$ is

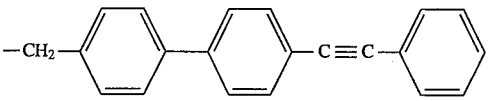

or a pharmaceutically acceptable salt thereof.

26. A method for treating or preventing the onset of Pneumocystis pneumonia in a host susceptible to Pneumocystis pneumonia which comprises administering an effective amount of a compound of formula I, or a pharmaceutically acceptable salt thereof, to a host in need of such treatment.

27. A method according to claim 26 where the compound is one where:

R', R" and R'" are each methyl;
$R^{y1}$, $R^{y2}$, $R^{y3}$ and $R^{y4}$ are each hydroxy;
$R^{x1}$ is hydrogen, hydroxy or —O—R;
R is methyl, benzyl, —$CH_2CHOHCH_2OH$, —$(CH_2)_b NR^{z1}R^{z2}$ or —$(CH_2)_2 POR^{z3}R^{z4}$;
b is 2, 3, 4, 5 or 6;
$R^{z1}$ and $R^{z2}$ are independently hydrogen or $C_1$–$C_4$ alkyl;
$R^{z3}$ and $R^{z4}$ are independently hydroxy or methoxy;

$R^{x2}$ is hydrogen or hydroxy;
$R^0$ is hydroxy or a group of the formulae:

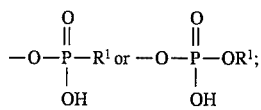

$R^1$ is methyl;
p-nitrophenyl, benzyl, p-halo-benzyl or p-nitro-benzyl;
or a pharmaceutically acceptable salt thereof.

28. A method according to claim 27 where the compound is one where:
$R^{x1}$ is hydroxy;
$R^{x2}$ is hydroxy;
$R^0$ is hydroxy;
$R^2$ is a group of the formula:

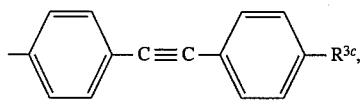

or

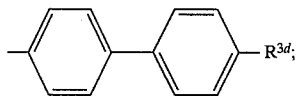

$R^{3c}$ and $R^{3d}$ are independently hydrogen, $C_2$–$C_{12}$ alkynyl, $C_1$–$C_{12}$ alkoxy or —O—$(CH_2)_m$—[O—$(CH_2)_n]_p$—O—($C_1$–$C_{12}$ alkyl);
or a pharmaceutically acceptable salt thereof.

29. The method according to claim 28 where the compound is one where:
$R^2$ is

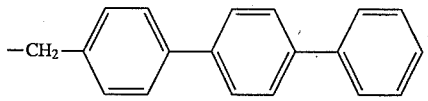

or a pharmaceutically acceptable salt thereof.

30. The method according to claim 28 where the compound is one where:
$R^2$ is

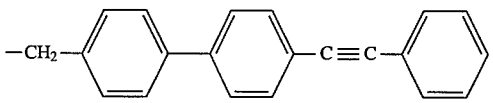

or a pharmaceutically acceptable salt thereof.

* * * * *

UNITED STATES PATENT AND TRADEMARK OFFICE
CERTIFICATE OF CORRECTION

PATENT NO. : 5,618,787
DATED : April 8, 1997
INVENTOR(S) : Jamison, et al.

It is certified that error appears in the above-indentified patent and that said Letters Patent is hereby corrected as shown below:

Column 7, line 49, "arm," should read, --art,--.
Column 19, line 13, delete the word "10".

Signed and Sealed this

Twenty-first Day of July, 1998

Attest:

Attesting Officer

BRUCE LEHMAN

Commissioner of Patents and Trademarks